United States Patent [19]
Baricevac et al.

[11] Patent Number: 4,636,090
[45] Date of Patent: Jan. 13, 1987

[54] LOW TEMPERATURE DILATOMETER

[75] Inventors: Thomas A. Baricevac, Bayside; Karl-Heinz Raffalski, Wheatley Heights, both of N.Y.

[73] Assignee: Theta Industries, Inc., Port Washington, N.Y.

[21] Appl. No.: 736,813

[22] Filed: May 22, 1985

[51] Int. Cl.[4] .................... G01N 25/16; G01N 3/08; G01K 1/14
[52] U.S. Cl. .................... 374/56; 374/50; 374/55; 374/208; 73/860
[58] Field of Search .................... 374/49–51, 374/55, 56, 208, 210; 73/856, 860, 790, 818; 269/224, 254, 254 CS, 254 MW; 24/459, 460, 462; 248/231.6, 231.8, 316.6, 316.7

[56] References Cited

U.S. PATENT DOCUMENTS

| | | | |
|---|---|---|---|
| 2,350,060 | 5/1944 | Montgomery | 269/224 |
| 2,351,572 | 6/1944 | Kingston | 374/55 |
| 3,494,527 | 2/1970 | Bauer et al. | 26/93 |
| 3,583,207 | 6/1971 | Ullman | 374/208 |
| 3,680,357 | 8/1972 | Clusener | 374/56 |
| 3,885,416 | 5/1975 | Cooper | 374/56 |
| 3,898,836 | 8/1975 | Clusener | 374/56 |
| 3,919,879 | 11/1975 | Betz | 374/56 |
| 4,351,615 | 9/1982 | Vettori de Almeida Rodrigues | 374/56 |

FOREIGN PATENT DOCUMENTS 705316  12/1979  U.S.S.R. ............... 374/55

*Primary Examiner*—Charles Frankfort
*Assistant Examiner*—W. Morris Worth
*Attorney, Agent, or Firm*—Burton E. Levin

[57] ABSTRACT

Low temperature dilatometers are described which employ a combination cryostat/furnace made from an elongated block of metal by drilling separate longitudinal tubular chambers for insertion of a specimen tube containing a specimen and at least one electric resistance heater. A separate longitudinally drilled tubular cooling chamber serves as the expansion chamber for a conventional compressed gas refrigeration system, one end of the cooling chamber communicating with the inlet of the refrigerant gas compressor and the other end communicating, through an intermediate heat exchanger, with the outlet of the compressor. The metal construction of the cryostat/furnace and the absence of a conventional ceramic protection tube for the specimen facilitates rapid heat transfer to and from the specimen. The specimen can be brought quickly to the minimum desired temperature by operating the refrigeration system until that temperature is reached and then shutting off the compressor. The temperature then can be raised at a controlled rate to the desired maximum by continuous or intermittant operation of the heater or by alternate operation of the heater and refrigeration system. High and low temperatures also may be cycled readily. Changes in the length of the specimen are transmitted through a ceramic pushrod to a linear variable differential transformer dilation sensor. Specimen holders are described which prevent flexible specimens from bending during dilation measurements.

11 Claims, 7 Drawing Figures

LOW TEMPERATURE DILATOMETER

BACKGROUND OF THE INVENTION

1. Field of the Invention

This invention relates generally to dilatometers, and, more particularly, to dilatometers which permit precise temperature control and accurate dilation measurements of a test specimen within the range of about −65° C. to about 150° C. or higher.

2. Description of the Prior Art

Dilatometers are analytical instruments that respond to the linear thermal expansion or contraction of solids. Generally, these instruments employ a variable temperature electric furnace in which the test specimen is heated at a programmed rate to a desired elevated test temperature. The test specimen, which commonly is from about 10 to about 50 mm in length, is held within such furnace between a flat surface on a stationary object and an opposing flat surface on a movable object, such as a ceramic pushrod, that extends outside the furnace. Temperature induced changes in the length of the specimen are transmitted through the rod to a dilation sensor, which can be a mechanical, optical or electrical system for amplifying and measuring that change. These instruments are useful for measuring specimen dilation within the range of from ambient temperature to the maximum temperature of the furnace, which commonly is about 1000° C. and often is as high as 1500° C. or more.

Among the least complicated dilatometers in common use are those in which the push rod is coupled to a dial gauge and the dilation of a specimen is read directly from that gauge. Such dial gauge dilatometers are simple to use and inexpensive, but generally are suitable only for low to moderately elevated temperature applications that do not demand great precision.

U.S. Pat. No. 3,680,357 describes a far more precise type of dilatometer in which the dilation sensor is a linear variable differential transformer which translates specimen dilation into electrical signals that can readily be amplified and recorded. In such sensor, the core floats freely in the coil and each of these elements is separately supported at its ends by a pair of compound cantilevered flat springs. These springs permit independent and frictionless axial movement of the suspended element, but restrain radial or transverse movement. This independent and frictionless axial mobility of the core and coil facilitates calibration of the sensor and renders it extremely sensitive to minute changes in specimen length, thereby making possible exceptionally accurate measurements of thermally induced expansion or contraction.

When such dilatometer is used with a single pushrod, as shown in FIG. 1 of the aforementioned Patent, that pushrod commonly is coupled to and supported only by the core of the linear variable differential transformer and it extends into the open end of a ceramic specimen tube, where it abuts a specimen that is held between a flat ground surface at the end of the pushrod and a similar flat ground surface on the interior of the other closed end of the specimen tube. An opening commonly is provided in the wall of the specimen tube adjacent to its closed end to facilitate specimen changes. The closed end of the specimen tube is inserted into a variable temperature furnace, which, for many applications, is a conventional electric tube furnace.

For measurements of the differential thermal expansion of two specimens, separate closely spaced pushrods may be coupled to the core and coil of the linear variable differential transformer and the equally closely spaced specimens are held abreast within a single tubular specimen tube that is inserted in a similar electric tube furnace, as shown by U.S. Pat. No. 3,898,836.

While the typical dilatometers described above generally are used for dilation measurements at elevated temperatures, they also can be used for measurements at temperatures below ambient by substituting a cryostat for the electric furnace. Exemplary of such low temperature dilatometers is the instrument described in U.S. Pat. No. 4,351,615, in which the specimen, enclosed in a protective fused silica tube, is immersed in a cryostat containing liquid helium. The temperature within the cryostat is raised for dilation measurements by an electric heating sleeve that surrounds the protective tube. In order to avoid a magnetic field influence on the specimen, the wire in the heating sleeve is wound "two wires in hand" after bending the wire in a loop thus forming two coils having compensating fields.

While this cryostat enables the user to achieve initial specimen temperatures which approach the −268.9° C. boiling point of helium, such extreme low temperatures are not essential for the great majority of dilation studies, which require minimum and maximum temperatures similar to those normally encountered by the material being tested. For example, military specifications for printed circuit boards and electronic devices on those boards call for an operating free-air temperature range of −55° to 125° C. and a storage temperature range of −65° to 150° C. Even these extreme ranges, which rarely, if ever, are actually experienced, are considerably higher than the boiling point of helium. For most materials destined for civilian applications, the temperature range of greatest interest is defined by the expected winter low and summer high, which, in a temperate climate, rarely is outside the range of from about −30° to about 45° C. Measurements at these far higher temperatures are delayed by the fact that all or essentially all of the liquid helium must be vaporized and vented from the cryostat before there can be any significant rise in the temperature of the specimen. This necessitates lengthy operation of the heating sleeve and extremely precise control in order to avoid building up excessive internal pressure while the liquid helium is being boiled off and also to avoid temperature surges thereafter.

Another disadvantage of the low temperature dilatometer of U.S. Pat. No. 4,351,615, as well as similar instruments employing liquid nitrogen cooled cryostats, is the fact that a conventional length specimen dilates so little over a narrow temperature range, such as that experienced in a temperate climate, that otherwise small sensor, amplifier and recorder errors are exaggerated. One may only partially compensate for this by lengthening the specimen, as any increase in the mass of the specimen increases the possibility of temperature differentials and a decrease in the thickness of the lengthened specimen may make it insufficiently rigid to withstand the compressive force imposed by the pushrod.

SUMMARY OF THE INVENTION

It is the broad object of this invention to provide an improved low temperature dilatometer which is simple, sturdy and reliable and on which dilation measurements can be made quickly over either a broad or narrow temperature range. A specific object is to provide such dilatometer with a combination cryostat/furnace which requires neither a specimen protection tube nor a liquified gas coolant and which permits the specimen temperature to be reduced quickly to as low as about −65° C. and then raised smoothly to as high as about 150° C. It is a further object to provide such dilatometer with specimen holders that permit the use of long flexible specimens, thereby increasing the precision of dilation measurements made over a narrow temperature range.

These objects and other advantages, which will be apparent from this specification, are achieved by the invention described below.

It now has been determined that (1) it is neither necessary nor desirable in low temperature dilatometry to initially reduce the temperature of the specimen to a level far below that at which measurements are to be taken, as is necessary when employing a liquid helium or nitrogen cooled cryostat and (2) precise dilation measurements can be made over a narrow temperature range by using an unconventional specimen shape. We have found that our low thermal mass combined cryostat/furnace, which is cooled by a conventional compressed gas refrigeration system and heated by a conventional electric resistance heater, can be cooled at a linear rate to the lowest desired measurement temperature and that it the temperature can be increased at a linear rate by application of heat or stepwise by balancing heating and refrigeration. These high and low temperatures can readily be cycled. We also have found that precise dilation measurements can be made over a narrow temperature range by using a long thin specimen and restraining the flexing of such otherwise flexible specimen.

One aspect of our invention is a low temperature dilatometer comprising a combined cryostat/furnace, a specimen tube partially insertable therein and a dilation sensor coupled to a pushrod that is adapted to engage a specimen within said specimen tube, said cryostat/furnace being a block of metal having integral therein (a) a tubular specimen chamber for receiving said specimen within said specimen tube, (b) at least one tubular heating chamber containing an electric resistance heating element and (c) at least one tubular cooling chamber within which a compressed refrigerant gas is expanded.

Another aspect of our invention, which is useful in our low temperature dilatometer as well as other dilatometers, is a dilatometer specimen holder comprising a fixed member adapted to firmly engage a first end of an elongated specimen and a movable member adapted to firmly engage a second end of said specimen, said movable member being further adapted to apply a tensive force to said specimen and to be coupled to a dilation sensor.

Still another aspect of our invention, which also is useful in our low temperature dilatometer as well as other dilatometers, is a dilatometer specimen holder comprising a pair of specimen grasping blocks having smooth surfaces adapted to abut opposing sides of an interposed elongated specimen with the ends of said specimen protruding beyond said blocks, and spring means for maintaining said blocks in contact with said specimen to slidably clamp and restrain flexing of said specimen when subjected to compressive force at said ends.

DESCRIPTION OF THE PREFERRED EMBODIMENTS

Figure 1:
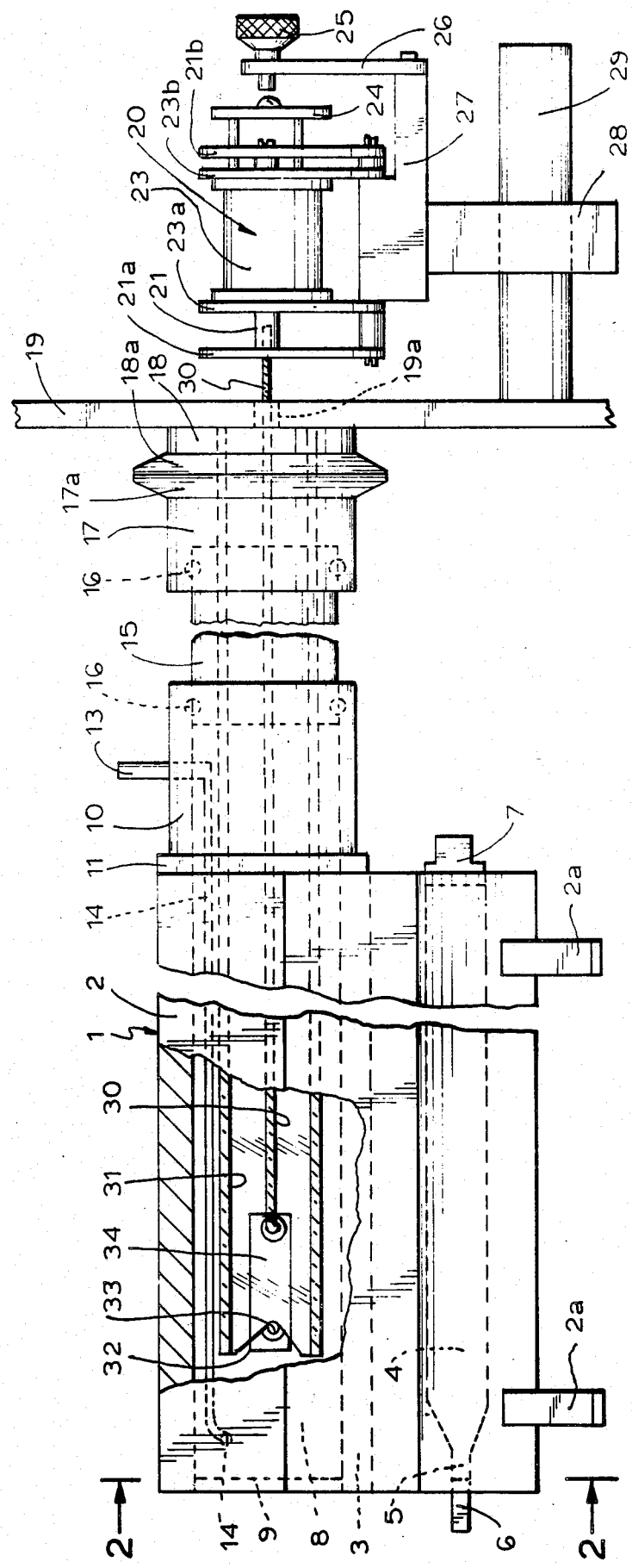
FIG. 1 is a side elevation of a low temperature dilatometer of this invention in which the dilation sensor is a linear variable differential transformer. This view is partially cut away to show a specimen holder of this invention.
Figure 2:
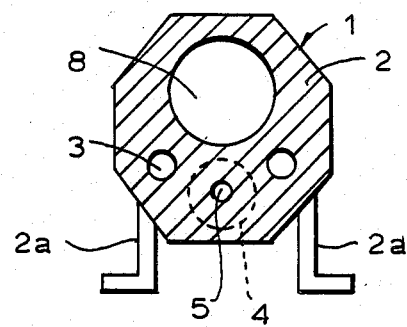
FIG. 2 is a partial cross-section along line 2—2 of FIG. 1 showing the combination cryostat/furnace.
Figure 3:
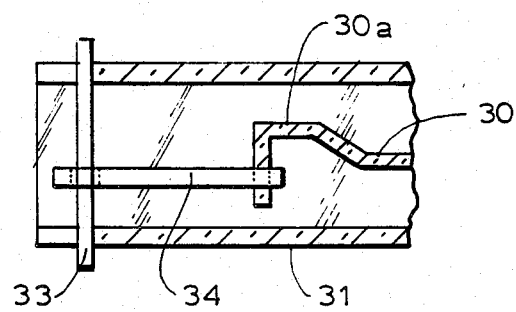
FIG. 3 is a plan view of the specimen holder of FIG. 1.

FIG. 1 illustrates a preferred embodiment of the low temperature dilatometers of this invention. The combined cryostat/furnace 1 includes an elongated block 2 which rests on mounting legs 2a and 2b. Block 2 has been made from a single length of two inch diameter octagonal aluminum bar which has been drilled longitudinally, as also shown in FIG. 2, to provide a tubular specimen chamber 8 for receiving one end of specimen tube 31, a pair of tubular heating chambers 3 for holding conventional electric resistance heaters (not shown) and a tubular cooling chamber 4, which serves as the expansion chamber for a compressed refrigerant gas, such as difluoro-dichloromethane, ammonia or sulfur dioxide, which can be introduced from any of a wide variety of commercially available low temperature refrigeration systems having single or multiple compression stages. Cooling chamber 4 has a restricted open end 5 holding a gas fitting 6 which delivers the compressed refrigerant gas from the outlet of such single or multi-stage compressor via an intermediate air or water cooled heat exchanger (neither shown). The other open end of cooling chamber 4 holds a second gas fitting 7 which communicates with the inlet of the compressor. Alternately, both gas fittings may be located at the same end of block 2 by positioning them at the open ends of a U-shape tubular metal expansion chamber which is inserted into cooling chamber 4. Insulation (not shown) advantageously covers block 2.

The solid metal construction of cryostat/furnace 1 eliminates the need for a ceramic protective tube, which conventionally encloses and insulates a dilatometer specimen, and facilitates rapid and uniform heat transfer to and from specimen 34, which has a thermocouple (not shown) welded to its surface for monitoring its temperature. The low thermal mass of cryostat/furnace 1 also moderates temperature surges and permits smooth temperature transitions.

Specimen chamber 8 is closed at one end by fused silica window 9, which permits the operator to visually observe specimen 34 within the notched open end 32 of specimen tube 31, which is partially inserted inserted into the other end of chamber 8. Specimen tube 31, which is firmly held at its other open end in the circular orafice of metal tube holder 18 on rigid upright pedistal 19, extends loosely through metal connecting ring 17, flexible tubing 15 and a second metal connecting ring 10 into specimen chamber 8. Tube holder 18 is demountably attached to connecting ring 17 by a ring clamp (not shown) that grasps flanges 18a and 17a. This demountable attachment permits the cryostat/furnace 1 to be moved away from metal tube holder 18, thereby exposing the notched end 32 of specimen tube 31 for specimen changes. Connecting ring 10 is attached through flange 11 to block 2 at the periphery of specimen chamber 8. The ends of flexible tubing 15 are inserted into connecting rings 10 and 17 and are sealed by rubber O-rings 16. Connecting ring 10 also is equipped with a gas fitting 13, through which a dry gaseous heat transfer medium, such as helium, is introduced into tube 14 and delivered to the vicinity of the specimen.

A fused silica rod 33, the ends of which rest in the notched end 32 of specimen tube 31, passes through a hole in one end of flexible strip specimen 34 and firmly holds that end. A fused silica hook 30a, which is attached to fused silica pushrod 30, passes through a hole at the other end of specimen 34. Pushrod 30 extends from hook 30a through a slightly larger diameter hole in upright pedistal 19 and is coupled to core 21 of a linear variable differential transformer dilation sensor 20 of the type described in U.S. Pat. No. 3,680,357. Core 21 is independently supported at its ends by a pair of compound cantilevered flat springs 21a and 21b which are attached through plate 27 to carriage 28. An opening through carriage 28 slidably engages mating post 29 and permits the carriage 28 and plate 27 to be moved toward or away from specimen 34. Since core 21 is coupled to specimen 34 through hook 30a and pushrod 30, movement of plate 27 away from specimen 34 causes flexing of springs 21a and 21b and imposes a tensive force on specimen 34. Dilation measurements made with the specimen under tension enables one to use long thin specimens which, without any lateral restraint as described below, would flex under a compressive force.

Coil 23 of dilation sensor 20 also is independently supported at its ends by a pair of compound cantilevered flat springs 23a and 23b which are attached throught plate 27 to carriage 28. These springs permit coil 23 and its yoke 24, which passes loosely through spring 21b, to be laterally displaced for calibration and electrical zeroing by a micrometer screw 25 that is held at its neck by a micrometer support 26 attached to plate 27. Micrometer screw 25 also can be used for electrical zeroing when dilation of a single specimen is being measured, as illustrated in FIG. 1. It, of course, can not be used for electrical zeroing when differential measurements are made on two specimens, as both the core and coil must remain movable.

For differential measurements, a second specimen having a size and shape the same as specimen 34 is held parallel and closely adjacent to specimen 34 by rod 33 and by a second fused silica hook and pushrod, which are similar to hook 30a and pushrod 30, but which are coupled to the coil 23, rather than the core 21. Movement of carriage 28 away from the specimens causes flexing of coil springs 23a and 23b and thereby also imposes a tensive force on the second specimen.

Figure 4:
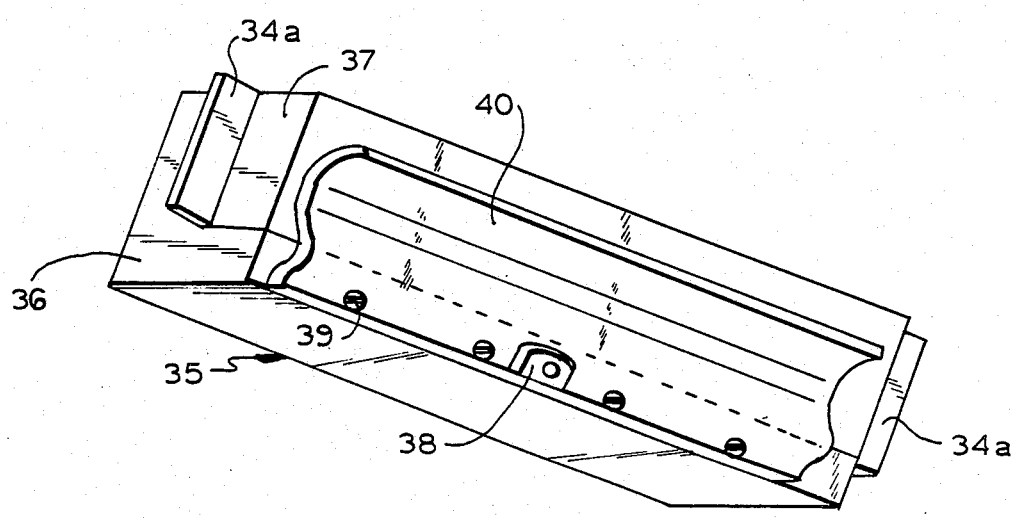
FIG. 4 is a perspective view of another specimen holder of this invention.
Figure 5:
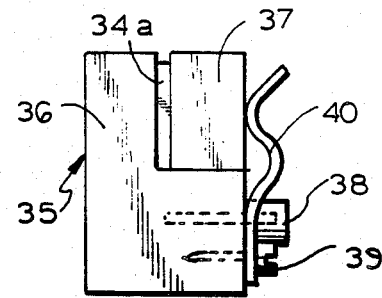
FIG. 5 is an end view of the specimen holder of FIG. 4.
Figure 6:
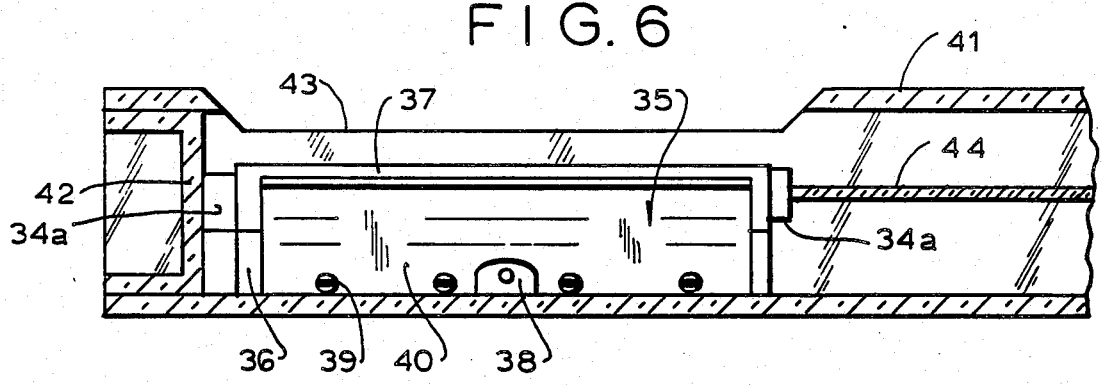
FIG. 6 is a side elevation of the specimen holder of FIG. 4 showing its position within a specimen tube.

While dilation measurements on a flexible specimen under tension, as described above, eliminates the possibility of error due to bending of the specimen, it often is advantageous to make such measurements when the specimen is being subjected to a compressive force. FIGS. 4 through 6 illustrate a specimen holder 35 which permits dilation measurements on specimens which, if laterally unrestrained, would bend when subjected to compressive forces. L-shaped elongated block 36 and an equal length rectangular block 37 abut the flat sides of strip specimen 34a, which protrudes at both ends from the blocks. Both are made of brass or other high heat conductivity material. All surfaces that contact the specimen are flat and smooth. Steel spring 40 is firmly attached by screws 39 to one leg of block 36 and presses block 37 toward the other leg, thus slidably grasping specimen 34a and restraining its flexing when compressive forces are imposed at its ends. A well 38 also is provided for insertion of a thermocouple.

As shown in FIG. 6, this holder is inserted through wall opening 43 into a conventional fused silica specimen tube 41 where it rests on the bottom with one of the protruding ends of specimen 34a abutting the flat interior surface of plug 42 and the other protruding end abutting the flat end of a conventional pushrod 44, which is coupled to a conventional dilation sensor. When holder 35, specimen tube 41 and pushrod 44 are substituted for the equivalent elements of FIG. 1 and pushrod 44 is coupled to core 21, movement of carriage 28 toward specimen 34a flexes springs 21a and 21b and imposes a compressive force on specimen 34a.

Figure 7:
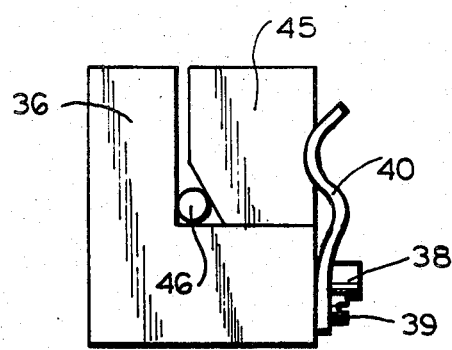
FIG. 7 is an end view of another specimen holder of this invention.

FIG. 7 shows a variation of the specimen holder of FIGS. 4 through 6 in which the rectangular block is modified to support a flexible wire specimen. In this embodiment, a corner of rectangular block 45 is flattened and smoothed so as to hold wire specimen 46 in the V-shape groove formed by the legs of L-shape block 36.

The flexure restraining specimen holders described above can be made to accomodate specimens of any desired length. When dilation measurements are made over a narrow range, such as from −30° C. to 45° C., it rarely is necessary that the specimen length greatly exceed about 50 mm.

It will, of course, be understood that various other additions and modifications may be made in the embodiments of this invention described above without departing from the spirit and scope of this invention as defined by the claims below.

We claim:

1. Low temperature dilatometer comprising a combination cryostat/furnace, a specimen tube having a closed end that is insertable into said cryostat/furnace, a specimen holder within said specimen tube and a dilation sensor coupled to a ceramic pushrod that is adapted to engage a specimen within said specimen tube,
   said cryostat/furnace being an elongated block of metal that has been drilled longitudinally to form a tubular specimen chamber for receiving said specimen within said specimen tube, at least one tubular heating chamber containing an electric resistance heating element and at least one tubular cooling chamber within which a compressed refrigerant is expanded and
   said specimen holder comprising a pair of specimen clamping blocks having smooth surfaces adapted to abut opposing sides of an interposed specimen with the ends of said specimen protruding beyond said blocks and spring means for maintaining said blocks in contact with said specimen to slidably grasp and restrain flexing said specimen, said closed end of said specimen tube being internally adapted to abut one said protruding specimen end and said push rod being adapted to abut the other said protruding specimen end and to apply a compressive force to said specimen.

2. Dilatometer of claim 1 wherein said smooth surfaces are flat and parallel and are adapted to abut the parallel flat sides of a strip specimen.

3. Dilatometer of claim 1 wherein at least one said smooth surface is a groove that is adapted to retain a wire specimen.

4. Dilatometer of claim 3 wherein one said smooth surface is a V-shape groove and the other said smooth surface is flat.

5. Dilatometer specimen holder comprising first and second specimen grasping blocks having smooth surfaces adapted to abut opposing sides of an interposed specimen with the ends of said specimen protruding beyond said blocks so as to be engagable by dilatometer force applying members, said first block having an L-shape cross-section with first and second legs forming a trough for retaining said second block and said second leg being attached to a spring clip adapted to urge said second block toward said first leg to slidably grasp said specimen between said blocks and restrain flexing of said specimen when subjected to compressive forces at said ends by said dilatometer force applying members.

6. Holder of claim 5 wherein said smooth surfaces are flat and parallel and are adapted to abut parallel flat sides of a strip specimen.

7. Holder of claim 5 wherein at least one said smooth surface is a groove that is adapted to retain a wire specimen.

8. Holder of claim 7 wherein one said smooth surface is a V-shaped groove and the other said smooth surface is flat.

9. Holder of claim 5 wherein one said block contains a thermocouple well.

10. Holder of claim 5 wherein said blocks are metal.

11. Holder of claim 5 wherein said blocks are elongated and of equal length.

* * * * *